United States Patent
Bertram et al.

(10) Patent No.: US 12,048,578 B2
(45) Date of Patent: Jul. 30, 2024

(54) DETERMINING A TARGET POSITION OF AN X-RAY DEVICE

(71) Applicants: Brainlab AG, Munich (DE); medPhoton GmbH, Salzburg (AT)

(72) Inventors: Michael Bertram, Markt Schwaben (DE); Robert Essenreiter, Munich (DE); Philipp Steininger, Jenbach (AT); Heinz Deutschmann, Salzburg (AT)

(73) Assignees: Brainlab AG, Munich (DE); medPhoton GmbH, Munich (DE)

( * ) Notice: Subject to any disclaimer, the term of this patent is extended or adjusted under 35 U.S.C. 154(b) by 0 days.

(21) Appl. No.: 17/580,723

(22) Filed: Jan. 21, 2022

(65) Prior Publication Data

US 2022/0142599 A1 May 12, 2022

Related U.S. Application Data

(63) Continuation of application No. 16/647,249, filed as application No. PCT/EP2019/050106 on Jan. 3, 2019, now Pat. No. 11,259,771.

(51) Int. Cl.
*A61B 6/00* (2024.01)
*A61B 6/46* (2024.01)
(Continued)

(52) U.S. Cl.
CPC ............... *A61B 6/547* (2013.01); *A61B 6/46* (2013.01); *A61B 6/584* (2013.01); *A61B 6/12* (2013.01);
(Continued)

(58) Field of Classification Search
CPC ........... A61B 6/547; A61B 6/46; A61B 6/584; A61B 6/12; A61B 6/4405; A61B 6/4441;
(Continued)

(56) References Cited

U.S. PATENT DOCUMENTS

| | | | |
|---|---|---|---|
| 6,714,810 B2 | 3/2004 | Grzeszczuk et al. | |
| 7,519,415 B2 * | 4/2009 | Mitschke | A61B 34/20 702/150 |

(Continued)

FOREIGN PATENT DOCUMENTS

| | | | | |
|---|---|---|---|---|
| DE | 102009025247 A1 * | 12/2010 | | A61B 6/12 |
| DE | 102014210897 A1 | 12/2015 | | |
| WO | 2011136988 A1 | 11/2011 | | |

OTHER PUBLICATIONS

Batkilin E et al:"Bone-mounted miniature robot for surgical procedures: concept and clinical applications", IEEE Transactions on Robotics and Automation, IEEE Inc, New York, US, vol. 19, No. 5,Oct. 1, 2003.

(Continued)

*Primary Examiner* — Sean D Mattson
(74) *Attorney, Agent, or Firm* — Tucker Ellis LLP (57) ABSTRACT

Disclosed is a computer-implemented method for determining a target position of an X-ray device which encompasses acquiring image data describing an anatomical structure of a patient, for example, by means of a 3D scan, and registering the image data relative to a coordinate system of the patient, for example by means of a navigation system (embodied by registered image data). Furthermore, a trajectory of an implant positioned within the anatomical structure relative to the patient coordinate system is acquired (embodied by trajectory data). A target position of an X-ray device for acquiring an X-ray image of at least part of the implant is determined based on the registered image and the acquired trajectory of the implant (embodied by X-ray device position data).

18 Claims, 5 Drawing Sheets

(51) Int. Cl.
*A61B 6/58* (2024.01)
*A61B 6/12* (2006.01)
*A61B 34/10* (2016.01)
*A61B 34/20* (2016.01)

(52) U.S. Cl.
CPC ....... *A61B 6/4405* (2013.01); *A61B 2034/107* (2016.02); *A61B 2034/2055* (2016.02)

(58) Field of Classification Search
CPC ...... A61B 2034/107; A61B 2034/2055; A61B 2090/376; A61B 34/20; A61N 5/10
See application file for complete search history.

(56) References Cited

U.S. PATENT DOCUMENTS

| | | | | |
|---|---|---|---|---|
| 11,259,771 | B2* | 3/2022 | Bertram | A61B 6/46 |
| 2010/0312103 | A1* | 12/2010 | Gorek | A61B 6/12 600/425 |
| 2013/0066196 | A1 | 3/2013 | Graumann et al. | |
| 2013/0083894 | A1 | 4/2013 | Niebler et al. | |
| 2014/0049629 | A1 | 2/2014 | Siewerdsen et al. | |
| 2015/0201892 | A1* | 7/2015 | Hummel | G06T 19/006 348/77 |
| 2016/0242724 | A1 | 8/2016 | Lavallee et al. | |
| 2017/0086759 | A1 | 3/2017 | Eichler et al. | |
| 2017/0290559 | A1* | 10/2017 | Gemmel | A61B 6/469 |
| 2017/0340394 | A1* | 11/2017 | Gemmel | A61B 6/5247 |
| 2017/0348056 | A1* | 12/2017 | Steinle | A61B 34/30 |

OTHER PUBLICATIONS

Ralf Westphal: "Sensor-based surgical Robotics: Contributions to Robot Assisted Fracture Healing", Internet Citation, Jul. 5, 2007 (Jul. 5, 2007), Retrieved from the Internet: URL:http://www.rob.cs.tu-bs.de/content/03-research/03-publications/download/rwe.
Browbank I et al:"Robotic-Assisted Internal Fixation of Hip Fractures: a Fluoroscopy-Based Intraoperative Registration Technique", Proceedings of the Institution of Mechanical Engineers.Journal of Engineering in Medicine. Part H, Mechanical Engineering Publications LTD, London, GB, vol. 214, No. Part H02, Jan. 1, 2000.
International Search Report and Written Opinion for corresponding international application No. PCT/EP2019/050106, dated Oct. 9, 2019.

* cited by examiner

DETERMINING A TARGET POSITION OF AN X-RAY DEVICE

RELATED APPLICATION DATA

This application is a continuation of application Ser. No. 16/647,249 filed Mar. 13, 2020 which is a national phase application of International Application No. PCT/EP2019/050106 filed Jan. 3, 2019, the contents of which are incorporated herein by reference.

FIELD OF THE INVENTION

The present invention relates to a computer-implemented method for determining a target position of an X-ray device, a corresponding computer program, a non-transitory program storage medium storing such a program and a computer for executing the program as well as a medical system comprising the aforementioned computer.

TECHNICAL BACKGROUND

Positioning an implant, for example a pedicle screw, in an anatomical structure of a patient with the help of a navigation system is nowadays commonly applied in the medical field. However, navigation of an implant may be prone to errors. For example, when using an optical navigation system the position of a reference, such as a marker device, on the patient may have been changed accidently during the navigation procedure.

Evaluating the final position of the implant within the anatomical structure of the patient is a crucial task. One approach is to take an image of the final position of the implant within the anatomical structure of the patient by means of a C-arm X-ray device for control purposes. However, manually positioning a C-arm X-ray device is a quite tedious procedure. In particular, finding a suitable imaging direction for appropriately checking the final position of the implant may be cumbersome. Moreover, several images may be necessary to find a suitable imaging direction for evaluating the final position of the implant. Accordingly, the radiation exposure of the patient may be increased.

The present invention has the object of providing an improved method for determining a target position of an X-ray device.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring image data describing an anatomical structure of a patient, for example, by means of a 3D scan, and registering the image data relative to a coordinate system of the patient, for example by means of a navigation system (embodied by registered image data). Furthermore, a trajectory of an implant positioned within the anatomical structure relative to the patient coordinate system is acquired (embodied by trajectory data). A target position of an X-ray device for acquiring an X-ray image of at least part of the implant is determined based on the registered image and the acquired trajectory of the implant (embodied by X-ray device position data).

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method for determining a target position of an X-ray device according to claim 1. The method comprises executing, on at least one processor of at least one computer, the following exemplary steps which are executed by the at least one processor.

In a (for example first) exemplary step, registered image data is acquired which describes a medical image of an anatomical structure of a patient relative to a coordinate system of a patient. Image data describing the medical image of the anatomical structure may be acquired by means of an imaging device (for example, by a 3D scan). The imaging device may be an X-ray device (for example a mobile X-ray device), for example a 3D computed tomography (CT) scanner, in particular a mobile 3D CT scanner. The image data may be acquired intra-operatively.

The image data may be registered to the coordinate system of the patient by means of a navigation system, in particular an optical navigation system, to acquire the registered image data. A (for example, first) reference, for example marker device, detectable by the navigation system may be attached to the patient, in particular to a vertebra of the patient, in order to define the coordinate system of the patient.

The imaging device may be provided with a (for example, second) reference, for example a marker device, detectable by the navigation system. The reference may be attached to the imaging device. Based on a known spatial relationship of the imaging device and the patient the image data may be registered to the coordinate system of the patient to acquire the registered image data.

In a (for example second) exemplary step, trajectory data is acquired which describes a trajectory of an implant positioned within the anatomical structure relative to the coordinate system of the patient. In one, embodiment, the implant may be a pedicle screw.

The trajectory may be described by a straight line in a three-dimensional coordinate system. In one example, the trajectory may comprise an entry point and a target point of the implant within the anatomical structure. The entry point and the target point may be endpoints of the trajectory. In one example, the trajectory may correspond at least partially to a longitudinal length of the implant.

In one embodiment, the trajectory data may be acquired during navigation of the implant, for example by means of the navigation system. In one example, a (for example, third) reference, for example a marker device, detectable by the navigation system may be attached to an instrument guiding the implant.

The trajectory data may comprise planned trajectory data which describes a planned trajectory of the implant. The trajectory data may be acquired intra-operatively or preoperatively. In one example, at least part of the trajectory data may be acquired during navigation of the implant along a planned trajectory.

In one embodiment, the trajectory data may be acquired automatically by a navigation system, i.e. the navigation system may save the trajectory automatically. In particular, the navigation system may save the trajectory after the implant is placed at its final position. In one example, the trajectory may be acquired after a user input to the navigation system.

In a (for example third) exemplary step, X-ray device position data is determined based on the trajectory data and the registered image data, wherein the X-ray device position data describes a target position of the X-ray device. In one example, the X-ray device may be a mobile X-ray device. In one embodiment, the X-ray device may be the imaging device, described above with regard to the step of acquiring registered image data. The X-ray device position data may describe the target position of the X-ray device relative to the coordinate system of the patient or relative to a coordinate system of the X-ray device. In one embodiment, the X-ray device position data may describe the position of the source and/or the position of the detector of the X-ray device.

By automatically determining a target position of the X-ray device, a tedious manual positioning of the X-ray device may be avoided. In one embodiment, X-ray device position data may be acquired, as described above, for a plurality of trajectories of a plurality of implants.

In one embodiment, the method may further comprise the following step: X-ray imaging direction data is acquired which describes an orientation of the imaging direction of the X-ray device relative to the orientation of the trajectory. Determining the X-ray position data may be further based on the X-ray imaging direction data.

The X-ray device may be pre-calibrated by means of a phantom. In other words, the imaging geometry of the X-ray device may be determined. The imaging direction of the X-ray device may be determined relative to a coordinate system of the X-ray device. In another embodiment, the image data may be registered directly to the x-ray device by means of a phantom in the image data during patient scan.

The X-ray device may be provided with a reference, for example a marker device, detectable by the navigation system. The reference may be attached to the X-ray device. Based on a known spatial relationship of the x-ray device and the patient the orientation of the imaging direction of the X-ray device may be associated to the orientation of trajectory of the implant (described by the X-ray imaging direction data).

The imaging direction of the X-ray device may be oriented along the orientation of the trajectory or within a predetermined angle range relative to the orientation of the trajectory. The angle range may range from 0° to 10°, in particular from 0° to 5°, for example from 0° to 2°. The imaging direction of the X-ray device may be oriented relative, for example parallel or perpendicular, to the orientation of the trajectory.

In one embodiment, the imaging direction of the X-ray device may be oriented along the longitudinal axis of the implant, for example a pedicle screw. In one embodiment, a source of the X-ray device may be directed to one end of the implant (for example, the tip of a pedicle screw) and a detector of the X-ray device may be directed to another end of the implant (for example, the head of a pedicle screw).

In one example, the method may further comprise the following step: control data is determined based on the X-ray device position data. The control data may describe a control signal for controlling at least one actuator of the X-ray device. The X-ray device or at least a part of the X-ray device, for example the source and/or the detector, may move automatically to the target position by means of the control data.

In one embodiment, the method may further comprise the following step: display output data is determined based on the X-ray device position data. The display output data may describe a display output associated with the target position of the X-ray device. For example, the display output may describe instructions for the user for positioning the X-ray device at the target position. The user may manually move the X-ray device or at least a part of the X-ray device to the target position in accordance with the display output.

The method may further comprise the following step: X-ray image data is acquired after the X-ray device is positioned at the target position described by the X-ray device position data. The X-ray image data may describe an X-ray image (for example, a 2D X-ray image) of at least a part of the anatomical structure comprising at least a part of the implant. Accordingly, the position of the implant within the anatomical structure may be evaluated by the user. For example, the position of a pedicle screw within the pedicle may be evaluated. In other words, the user may evaluate if the pedicle screw is positioned correctly within the pedicle by means of the X-ray image. If the pedicle screw is positioned incorrectly, for example perforates the pedicle or the spinal cord, the screw may be repositioned directly.

In case the imaging direction of the X-ray device is oriented along a longitudinal direction of the implant, evaluation of the position of the implant may be simplified for the user. The user may then easily evaluate if the implant is positioned correctly within the anatomical structure, for example if the pedicle screw is positioned correctly within the pedicle.

In one embodiment, the X-ray image data may be acquired for a plurality of implants. The X-ray image data may be output to a screen with or without additional information.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect or according to the second aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system for acquiring an X-ray image of at least part of an implant within an anatomical structure, comprising:
 a) the at least one computer according to the fourth aspect;
 b) a navigation system;
 c) an X-ray device,
 wherein the at least one computer is operably coupled to the navigation system and the X-ray device.

For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to determining a target position of an X-ray device. For this reason alone, no surgical or therapeutic activity and in particular no surgical or therapeutic step is necessitated or implied by carrying out the invention.

The present invention also relates to a use of the system according to the fifth aspect for acquiring an X-ray image of at least part of an implant within an anatomical structure, wherein the use comprises execution of the steps of the method according the first aspect.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, Ill-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired.

The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:
1. "An Efficient and Accurate Camera Calibration Technique for 3D Machine Vision", Roger Y. Tsai, Proceedings of the IEEE Conference on Computer Vision and Pattern Recognition. Miami Beach, Florida, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. US 61/054,187

Shape representatives represent a characteristic aspect of the shape of an anatomical structure. Examples of shape representatives include straight lines, planes and geometric figures. Geometric figures can be one-dimensional such as for example axes or circular arcs, two-dimensional such as for example polygons and circles, or three-dimensional such as for example cuboids, cylinders and spheres. The relative position between the shape representatives can be described in reference systems, for example by co-ordinates or vectors, or can be described by geometric variables such as for example length, angle, area, volume and proportions. The characteristic aspects which are represented by the shape representatives are for example symmetry properties which are represented for example by a plane of symmetry. Another example of a characteristic aspect is the direction of extension of the anatomical structure, which is for example represented by a longitudinal axis. Another example of a characteristic aspect is the cross-sectional shape of an anatomical structure, which is for example represented by an ellipse. Another example of a characteristic aspect is the surface shape of a part of the anatomical structure, which is for example represented by a plane or a hemisphere. For example, the characteristic aspect constitutes an abstraction of the actual shape or an abstraction of a property of the actual shape (such as for example its symmetry properties or longitudinal extension). The shape representative for example represents this abstraction.

Determining the position is referred to as referencing if it implies informing a navigation system of said position in a reference system of the navigation system.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
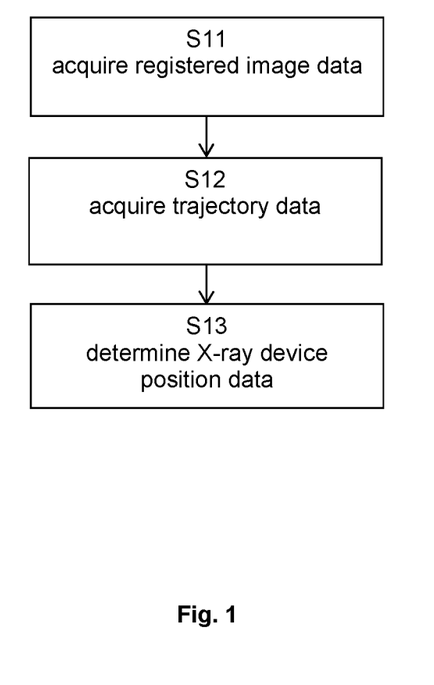
FIG. 1 is a flow diagram illustrating the basic steps of the method for determining a target position of an X-ray device.

FIG. 1 illustrates the basic steps of the method for determining a target position of an X-ray device according to the first aspect, in which step S11 encompasses acquisition of the registered image data and step S12 encompasses acquisition of the trajectory data. The subsequent step S13 encompasses determining the X-ray device position data.

Figure 2:
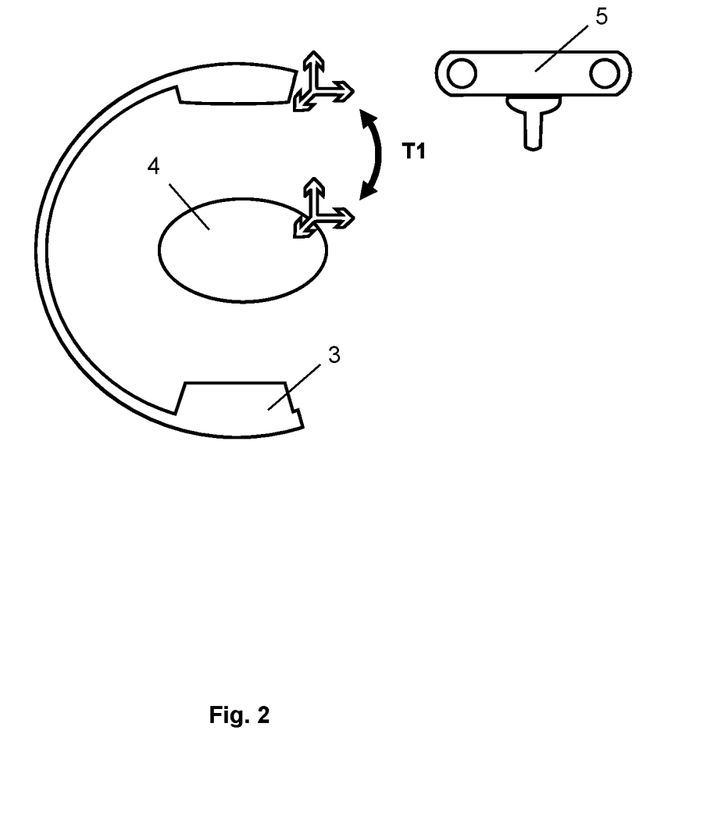
FIG. 2 is a schematic illustration of acquiring registered image data of an anatomical structure of a patient.

FIG. 2 is a schematic illustration of acquiring registered image data of an anatomical structure of a patient 4. Medical image data is acquired by an imaging device (for example by means of a 3D scan). The imaging device may be for example an X-ray device 3, as shown in FIG. 2.

A first reference (not shown), for example a first marker device, is attached to the patient 4, for example attached to a vertebrae of the patient 4. A second reference (not shown), for example a second marker device, is attached to the imaging device, here the X-ray device 3. The first reference and the second reference are detectable (for example trackable) by a navigation system 5, for example an optical navigation system.

Figure 5:
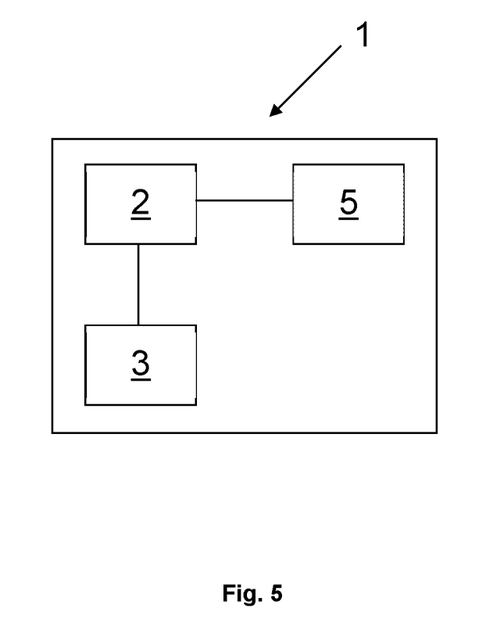
FIG. 5 is a schematic illustration of the system according to the fifth aspect.

The X-ray device 3 and the navigation system 5 are connected to a computer 2 (as shown in FIG. 5). The connection may be wired or wireless. Based on the known spatial relationship between the first reference attached to the patient 4 and the second reference attached to the X-ray device 3, the image data acquired by the X-ray device 3 may be registered via a transformation matrix T1 relative to a coordinate system of the patient 4.

Figure 3:
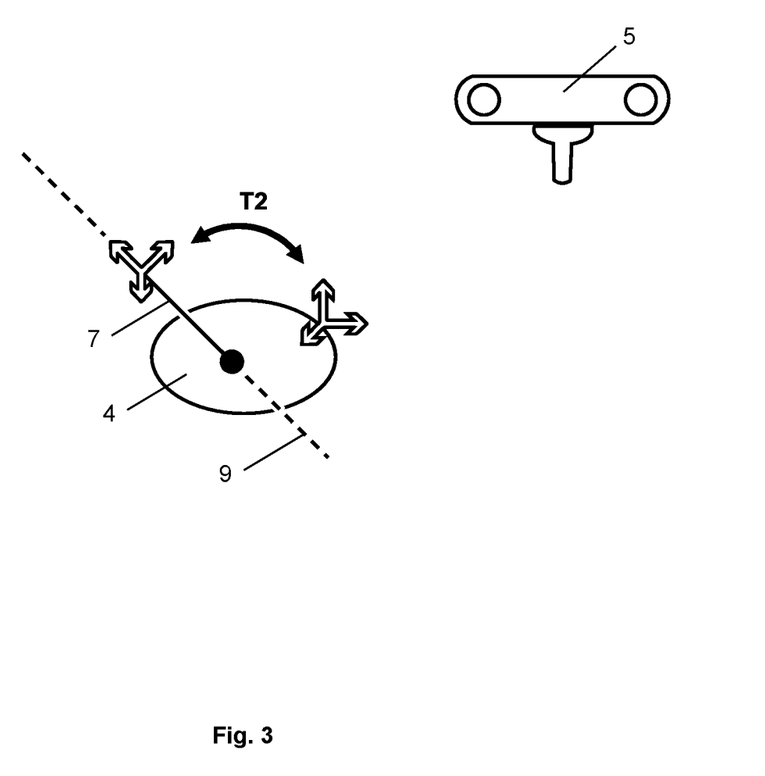
FIG. 3 is a schematic illustration of positioning an implant within the anatomical structure of the patient.

FIG. 3 is a schematic illustration of positioning an implant 7 within the anatomical structure of the patient 4. In one example, the implant 7 is a pedicle screw positioned within a pedicle of the patient 4. Positioning of the implant 7 is navigated (tracked) by the navigation system 5. In one example, a third reference, for example a marker device, is attached to an instrument guiding the implant 7.

As shown, in FIG. 3 a trajectory 9 of the implant (described by trajectory data) is acquired by the navigation system 5. The trajectory 9 of the implant 7 is indicated by the dashed line in FIG. 3. The trajectory 9 comprises an entry point and a target point of the implant 7 within the anatomical structure of the patient 4. In one example, the implant 7 may be guided along a (for example, preoperatively) planned trajectory and the (actual) trajectory may be acquired during navigation.

Based on the known spatial relationship between the implant 7 and the patient 4 the trajectory data may be registered via a transformation matrix T2 relative to the coordinate system of the patient 4. The trajectory data may be saved automatically by the navigation system 5 after positioning of the implant 7. The trajectory data of a plurality of implants 7 may be acquired consecutively.

Figure 4:
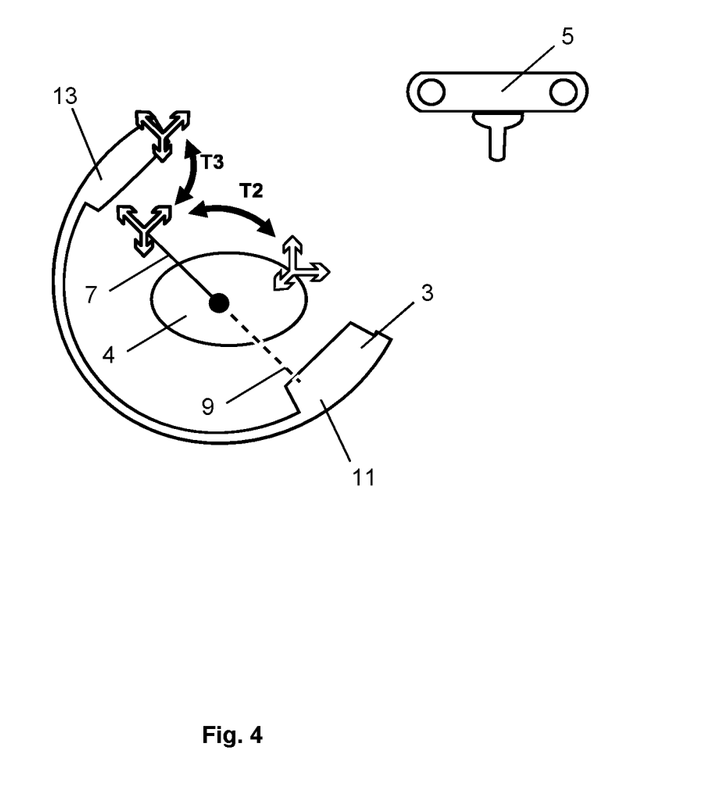
FIG. 4 is a schematic illustration of positioning the X-ray device at a target position.

FIG. 4. is a schematic illustration of positioning the X-ray device 3 at a target position.

Based on the known spatial relationship between the X-ray device 3 and the implant 7 the trajectory data of the implant 7 may be registered via the transformation matrix T3 relative to the coordinate system of the X-ray device 3. Based on the registered image data and the trajectory data a target position (described by the X-ray device position data) of the X-ray is determined for acquiring a (control) image of the implant 7.

In the target position the imaging direction of the X-ray device 3 may be oriented along the orientation of the trajectory of the implant 7. As shown in FIG. 4, the imaging direction of the X-ray device 3 may be oriented along the longitudinal axis of the implant 7. For example, a source 11 of the X-ray device 3 may be directed to one end of the implant 7 (for example, the tip of a pedicle screw) and a detector 13 of the X-ray device may be directed to another end of the implant (for example, the head of a pedicle screw).

Accordingly, a (control) image at least part of the implant 7 may be acquired, which allows an easy evaluation of position of the implant 7 within the anatomical structure. In case of a plurality of implants 7 a plurality of (control) images may be acquired consecutively.

FIG. 5 is a schematic illustration of the medical system 1 according to the fifth aspect. The system is in its entirety identified by reference sign 1 and comprises the computer 2 with an electronic data storage device (not shown), for example a hard disc, the X-ray device 3 and the navigation system 5. The components of the medical system 1 have the functionalities and properties explained above with regard to the fifth aspect of this disclosure.

The invention claimed is:

1. A method in a navigation system for automatically determining a target position of an associated X-ray device, the method comprising:
   receiving patient image data acquired by an associated patient imaging device imaging an associated patient, wherein the patient image data is representative of an anatomical structure of the associated patient;
   registering the patient image data to a coordinate system of the associated patient as registered patient image data by:
      imaging a first marker device detectable by the navigation system, the first marker device being disposed on the associated patient;
      imaging a second marker device detectable by the navigation system, the second marker device being disposed on the associated patient imaging device;
      determining a spatial relationship between the associated patient imaging device and the associated patient based on the imaging of the first and second marker devices detectable by the navigation system; and
      using the determined spatial relationship to register the received patient image data with the coordinate system of the associated patient;
   receiving implant trajectory data that describes in the coordinate system of the associated patient a trajectory along a longitudinal direction of an associated implant device received in the anatomical structure of the associated patient;
   determining X-ray device position data based on the registered patient image data and the implant trajectory data, wherein the X-ray device position data describes the target position of the associated X-ray device whereat positions of a source and/or a detector of the associated X-ray device are oriented along the trajectory of the associated implant device to enable a user to evaluate if the implant device is positioned correctly within the anatomical structure; and
   determining control data based on the X-ray device position data, wherein the control data is representative of a control signal usable to cause the associated X-ray device to move automatically to the target position.

2. The method according to claim 1, wherein the receiving implant trajectory data comprises:
   imaging a third marker device detectable by the navigation system, the third marker device being attached to an associated instrument used to guide the associated implant device to a desired location relative to the anatomical structure of the associated patient.

3. The method according to claim 1, wherein the receiving implant trajectory data comprises:
   receiving planned trajectory data as the implant trajectory data from an associated user operating the navigation system, wherein the planned trajectory data describes a planned trajectory of the associated implant device relative to the anatomical structure of the associated patient.

4. The method according to claim 3, wherein the receiving the planned trajectory data as the implant trajectory data from the associated user operating the navigation system comprises:
   receiving planned trajectory data that describes an entry point and a target point of the associated implant device relative to the anatomical structure of the associated patient.

5. The method according to claim 1, wherein the receiving patient image data comprises receiving patient image data acquired by the associated X-ray device.

6. The method according to claim 1, wherein the receiving patient image data comprises receiving patient image data acquired by a further associated device different than the associated X-ray device.

7. A navigation system comprising:
a memory device;
logic stored in the memory device; and
a processor operable to execute the logic to automatically determine a target position of an associated X-ray device by:
receiving patient image data acquired by an associated patient imaging device imaging an associated patient, wherein the patient image data is representative of an anatomical structure of the associated patient;
registering the patient image data to a coordinate system of the associated patient as registered patient image data by:
imaging a first marker device detectable by the navigation system, the first marker device being disposed on the associated patient;
imaging a second marker device detectable by the navigation system, the second marker device being disposed on the associated patient imaging device;
determining a spatial relationship between the associated patient imaging device and the associated patient based on the imaging of the first and second marker devices detectable by the navigation system; and
using the determined spatial relationship to register the received patient image data with the coordinate system of the associated patient;
receiving implant trajectory data that describes in the coordinate system of the associated patient a trajectory along a longitudinal direction of an associated implant device received in the anatomical structure of the associated patient;
determining X-ray device position data based on the registered patient image data and the implant trajectory data, wherein the X-ray device position data describes the target position of the associated X-ray device whereat positions of a source and/or a detector of the associated X-ray device are oriented along the trajectory of the associated implant device to enable a user to evaluate if the implant device is positioned correctly within the anatomical structure; and
determining control data based on the X-ray device position data, wherein the control data is representative of a control signal usable to cause the associated X-ray device to move automatically to the target position.

8. The navigation system according to claim 7, wherein the processor is operable to execute the logic to receive the implant trajectory data by:
imaging a third marker device detectable by the navigation system, the third marker device being attached to an associated instrument used to guide the associated implant device to a desired location relative to the anatomical structure of the associated patient.

9. The navigation system according to claim 7, wherein the processor is operable to execute the logic to receive the implant trajectory data by:

receiving planned trajectory data as the implant trajectory data from an associated user operating the navigation system, wherein the planned trajectory data describes a planned trajectory of the associated implant device relative to the anatomical structure of the associated patient.

10. The navigation system according to claim 9, wherein the processor is operable to execute the logic to receive the planned trajectory data as the implant trajectory data from the associated user operating the navigation system by:
receiving planned trajectory data that describes an entry point and a target point of the associated implant device relative to the anatomical structure of the associated patient.

11. The navigation system according to claim 7, wherein the processor is operable to execute the logic to receive the patient image data by receiving patient image data acquired by the associated X-ray device.

12. The navigation system according to claim 7, wherein the processor is operable to execute the logic to receive the patient image data by receiving patient image data acquired by a further associated device different than the associated X-ray device.

13. A computer readable medium storing instructions thereon that are executable by a processor to perform a method for automatically determining a target position of an associated X-ray device, the method comprising:
receiving patient image data acquired by an associated patient imaging device imaging an associated patient, wherein the patient image data is representative of an anatomical structure of the associated patient; registering the patient image data to a coordinate system of the associated patient as registered patient image data by:
imaging a first marker device detectable by a navigation system, the first marker device being disposed on the associated patient;
imaging a second marker device detectable by the navigation system, the second marker device being disposed on the associated patient imaging device;
determining a spatial relationship between the associated patient imaging device and the associated patient based on the imaging of the first and second marker devices detectable by the navigation system; and
using the determined spatial relationship to register the received patient image data with the coordinate system of the associated patient;
receiving implant trajectory data that describes in the coordinate system of the associated patient a trajectory along a longitudinal direction of an associated implant device received in the anatomical structure of the associated patient;
determining X-ray device position data based on the registered patient image data and the implant trajectory data, wherein the X-ray device position data describes the target position of the associated X-ray device whereat positions of a source and/or a detector of the associated X-ray device are oriented along the trajectory of the associated implant device to enable a user to evaluate if the implant device is positioned correctly within the anatomical structure; and
determining control data based on the X-ray device position data, wherein the control data is representative of a control signal usable to cause the associated X-ray device to move automatically to the target position.

14. The computer readable medium according to claim 13, wherein the receiving implant trajectory data comprises:

imaging a third marker device detectable by the navigation system, the third marker device being attached to an associated instrument used to guide the associated implant device to a desired location relative to the anatomical structure of the associated patient.

15. The computer readable medium according to claim 13, wherein the receiving implant trajectory data comprises:

receiving planned trajectory data as the implant trajectory data from an associated user operating the navigation system, wherein the planned trajectory data describes a planned trajectory of the associated implant device relative to the anatomical structure of the associated patient.

16. The computer readable medium according to claim 15, wherein the receiving the planned trajectory data as the implant trajectory data from the associated user operating the navigation system comprises:

receiving planned trajectory data that describes an entry point and a target point of the associated implant device relative to the anatomical structure of the associated patient.

17. The computer readable medium according to claim 13, wherein the receiving patient image data comprises receiving patient image data acquired by the associated X-ray device.

18. The computer readable medium according to claim 13, wherein the receiving patient image data comprises receiving patient image data acquired by a further associated device different than the associated X-ray device.

* * * * *